(12) United States Patent
Bystritsky

(10) Patent No.: US 8,086,296 B2
(45) Date of Patent: *Dec. 27, 2011

(54) METHODS FOR MODIFYING ELECTRICAL CURRENTS IN NEURONAL CIRCUITS

(75) Inventor: Alexander Bystritsky, Sherman Oaks, CA (US)

(73) Assignee: Brainsonix Corporation, Sherman Oaks, CA (US)

( * ) Notice: Subject to any disclaimer, the term of this patent is extended or adjusted under 35 U.S.C. 154(b) by 853 days.

This patent is subject to a terminal disclaimer.

(21) Appl. No.: 11/895,687

(22) Filed: Aug. 27, 2007

(65) Prior Publication Data

US 2007/0299370 A1    Dec. 27, 2007

Related U.S. Application Data

(63) Continuation-in-part of application No. 10/135,137, filed on Apr. 30, 2002, now Pat. No. 7,283,861.

(51) Int. Cl.
*A61B 5/055* (2006.01)
(52) U.S. Cl. .......................... 600/411; 600/439
(58) Field of Classification Search ............... 600/411, 600/427, 439; 601/2–3
See application file for complete search history.

(56) References Cited

U.S. PATENT DOCUMENTS

| | | | |
|---|---|---|---|
| 4,343,301 A | 8/1982 | Indech | |
| 5,247,935 A | 9/1993 | Cline et al. | |
| 5,275,165 A | 1/1994 | Ettinger et al. | |
| 5,291,890 A | 3/1994 | Cline et al. | |
| 5,323,779 A | 6/1994 | Hardy et al. | |
| 5,476,438 A | 12/1995 | Edrich et al. | |
| 6,066,123 A * | 5/2000 | Li et al. | 604/507 |
| 6,088,613 A * | 7/2000 | Unger | 600/420 |
| 6,094,598 A | 7/2000 | Elsberry et al. | |
| 6,198,956 B1 | 3/2001 | Dunne | |
| 6,198,958 B1 | 3/2001 | Ives et al. | |
| 6,267,734 B1 | 7/2001 | Ishibashi et al. | |
| 6,348,793 B1 * | 2/2002 | Balloni et al. | 324/309 |
| 6,413,216 B1 * | 7/2002 | Cain et al. | 600/439 |
| 6,612,988 B2 | 9/2003 | Maor et al. | |
| 7,427,265 B1 * | 9/2008 | Keilman et al. | 600/300 |
| 7,505,807 B1 * | 3/2009 | Kucharczyk et al. | 600/411 |
| 2002/0127230 A1 * | 9/2002 | Chen | 424/178.1 |

OTHER PUBLICATIONS

Roth et al., "Deep Brain Stimulation in Neuropsychiatric Disorders," Current Psychiatry Report, vol. 3 (No. 5), p. 366-372, (Oct. 2001).
Barlow et al., "The Risk of Seizures after Receipt of Whole-Cell Pertussis or Measles, Mumps, and Rubella Vaccine," New England Journal of Medicine, vol. 345 (No. 9), p. 656-661, (Aug. 30, 2001).

(Continued)

*Primary Examiner* — Brian Casler
*Assistant Examiner* — Jonathan Cwern
(74) *Attorney, Agent, or Firm* — Pillsbury Winthrop Shaw Pittman LLP (57) ABSTRACT

Disclosed herein are methods for modifying electrical currents in brain circuits through the simultaneous use of focused ultrasound pulse (FUP) and an existing brain-imaging system, such as a functional magnetic resonance imaging (fMRI) system. The methods are used for research, treatment and diagnosis of psychiatric, neurological, and neuroendocrine disorders whose biological mechanisms include brain circuits. The methods include the simultaneous steps of applying FUP to a live neuronal circuit within a brain and monitoring a brain image produced by a brain imaging system during the application of FUP.

28 Claims, 4 Drawing Sheets

OTHER PUBLICATIONS

George et al., "Transcranial Magnetic Stimulation: A Neuropsychiatric Tool for the 21st Century," Journal of Neuropsychiatry and Clinical Neuroscience, vol. 8 ( No. 4), p. 373-382, (Fall 1996).

Clement et al., "A hemispher array for non-invasive brain therapy and surgery," Physics in Medicine & Biology, vol. 45 ( No. 12), p. 3707-3719, (Dec. 2000).

Rauch et al., "Clinical Neuroimaging in Psychiatry," Harvard Review of Psychiatry, vol. 2 ( No. 6), p. 297-312, (Mar./Apr. 1995).

Journal of Neural Engineering, "Towards multifocal ultrasonic neural stimulation: pattern generation algorithms," Hertzberg et al., vol. 7, 2010, 9 pages.

Science, New Series, Production of Reversible Changes in the Central Nervous System by Ultrasound, Fry et al., vol, 127, No, 3289, Jan. 10, 1958, pp. 83-84.

U.S. in Neurological Research, "Use of Intense Ultrasound in Neurological Research," W. J. Fry, M.S., pp. 143-147, 1958.

Ultrasonics, "Use of focused ultrasound for stimulation of nerve structures", L.R. Gavrilov, pp, 132-138, 1984.

Ultrasound in Med. & Biol., "Application of Focused Ultrasound for the Stimulation of Neural Structures," Gavrilov et al., 1996, vol. 22, No. 2, pp. 179-192.

The Journal of the Acoustical Society of America, "Ultrasonic Exposure Thresholds for Changes in Cells and Tissues," C. R. Hill, vol. 52, No. 2(part 2), pp. 667-672, 1971.

Ultrasound in Med. & Biol., "Focused Ultrasound Effects on Nerve Action Potential in Vitro," Colucci et al., vol. 35, No. 10, 2009, pp. 1737-1747.

Experimental Neurology, "Effects of Focused Ultrasonic Radiation on Peripheral Nerve, with Observations on Local Heating," P.P. Lele, vol. 8, 1963, pp. 47-83.

J. Acoust. Soc. Am., "Release of serotonin from human platelets by acoustic microstreaming," A. R. Williams, vol. 56, No. 5, Nov. 1974, pp. 1640-1643.

The Journal of the Acoustical Society of America, "Mechanisms for Nonthermal Effects of Sound," W. L. Nyborg, vol. 44, No. 5, 1968, pp. 1302-1309.

Ultrasonic Neurostimulation, "Remote Excitation of Neuronal Circuits Using Low-Intensity, Low-Frequencv Ultrasound," Tyler et al., vol. 3, No. 10, Oct. 2008, p. 1-11.

The Neuroscientist, "Noninvasive Neuromodulation with Ultrasound? A Continuum Mechanics Hypothesis," W. J. Tyler, XX(X), Jan. 25, 2010, pp. 1-12.

Ultrasonics, "In vitro effects of ultrasound with different energies on the conduction properties of neural tissue," Po-Hsiang Tsui et al., vol. 43, 2005, pp. 560-565.

Ultrasound in Med. & Biol., "Ultrasound-Induced Changes in Rates of Influx and Efflux of Potassium Ions in Rat Thyocytes in Vitro," Chapman et al., vol. 6, pp. 47-49, 1973.

* cited by examiner

METHODS FOR MODIFYING ELECTRICAL CURRENTS IN NEURONAL CIRCUITS

RELATED APPLICATIONS

This application is a continuation-in-part of application Ser. No. 10/135,137 utility Publication No. 2003/0204135, filed on Apr. 30, 2002, now U.S. Pat. No. 7,283,861.

BACKGROUND

1. Field of the Invention

The present invention relates to methods for medical diagnosis and treatment, and more particularly to methods for diagnosis and treatment of specific psychiatric, neurological and neuroendocrine conditions using a Focused Ultrasonic Pulse (FUP) delivered to different points of neuronal circuits within the brain using existing focused ultrasound devices. The treatment is performed under the guidance of the existing brain-imaging devices, such as functional magnetic resonance imaging (fMRI).

2. Brief Description of the Prior Art

With advances in brain imaging techniques, the pathophysiology of psychiatric and medical disorders began to be more and more related to the specific neuronal circuits. Neuronal circuits are specific brain centers functionally and anatomically connected with each other. Usually a circuit involves sub-cortical neuronal centers connected with cortex. It is not totally clear how the circuits operate. However, it is clear that they play a major role in multiple psychiatric, neurological and medical conditions. For example, Obsessive Compulsive Disorder (OCD) and OCD Spectrum Disorders including Impulse Control Disorders appear to be related to abnormality in Orbito-Fronto-Talamic-Striatum circuit. Panic Disorder, Social Anxiety Disorder and panic spectrum disorders seem to be associated with the abnormal functioning of circuit involving Orbital-Frontal cortex, Amygdala, Cingulum and Hippocampus. Post-Traumatic Stress Disorders seem to associate with Prefrontal Cortex, Amydgala and Hippocampus abnormalities. Psychotic disorders seem to have an association with Prefrontal Cortex-Talamic-Striatum and Occipital Cortex Circuits. Circuits involved in neurological conditions have also been identified. For example, Parkinsonian Disease, Huntington Chorea, La Touretts and tick syndromes seem to have abnormalities in Cortico-Talamic-Straitum Circuit. Chronic pain has association with corticothalamic circuits. Insomnia has association with temporal cortex-lymbic-cingulum circuit. Medical conditions seem to have connection with specific neurocircuitry. For example, obesity and stress are associated with temporal-hypothalamic circuit. For a simple review and description of the above circuits, see Clark, D. L. and Boutros, N. N., *Brain and Behavior* (1999) and Rauch, S. L. et al., "Clinical Neuroimaging in Psychiatry" in *Harvard Review of Psychiatry* (1995), Vol. 2, no. 6, pp. 297-312.

Neuroimaging techniques exist that permit assessment of rapid changes in activity of the brain. Functional Nuclear Magnetic Resonance (fMRI), Vector Electroencephalagraphy (V-EEG) and Positron Emission Tomography (PET) are the most promising. These techniques, specifically fMRI, are capable of producing real time 3-dimensional maps of brain activity. These techniques merit scientists to study the neuronal circuits involved in pathology of different psychiatric or neurological conditions. However, the study process has been slowed by the absence of reliable activation of these circuits.

Recently, a few novel methods of the treatment of mental and neurological disorders directed at neuronal circuits have been introduced. These include deep brain stimulation by implanted electrodes, successfully used in OCD, Parkinson's disease and epilepsy, and brain surgery used in the treatment of OCD and depression. See *New England Journal of Medicine* (Sep. 27 2001), pp. 656-63; R. M. Roth, et al., *Current Psychiatry Report* (October 2001), Vol. 3, no. 5, pp. 366-72. Because of the invasiveness and possible complications, these methods are reserved for the treatment resistant conditions where other treatments fail. However, the success of these treatments underlines the importance of specific neurocircuits in the pathophysiology of mental and neurological disorders. Furthermore, it underlines the importance of developing non-invasive methods of intervention at the neuronal circuit level. In addition, the studies using deep brain stimulation techniques determined that low frequency (2-150 Hz) signals inhibit the neuronal tissue and that high frequency (1-3 MHz) signals stimulate neuronal circuits.

Recently it has been proposed that neuronal circuits can be assessed and modified non-invasively using Transcranial Magnetic Stimulation (TMS). The signal from the brain after the TMS stimulation can be read using MRI. That method has been described in U.S. Pat. No. 6,198,958, incorporated herein by reference, which described using the method for therapeutic purposes. The method and device proposed by that patent are currently being implemented in psychiatry and neurology for diagnostic and therapeutic purposes. See M. S. George, et al., *Journal of Neuropsychiatry and Clinical Neuroscience* (Fall 1996), Vol. 8, no. 4, pp. 373-382. The method, however, has several problems. For example, TMS does not stimulate deep brain centers, because it is incapable of penetrating brain tissue deeper than 1-2 cm. Also, TMS has a large area of focus, 1 cubic cm or more, which does not permit focused activation of a specific neuronal circuit. Also, there is a problem in using TMS together with fMRI, because TMS produces a magnetic signal that interferes with the magnetic field and consequently with the fMRI image.

Focused ultrasound has been used to modify electrical currents in neuronal tissue. This has been done by a combined application of a magnetic field and an ultrasonic field to neuronal and other tissue in the body. The prior art proposes that modification of electrical currents in neuronal tissue will come from the interaction of the two fields. For example, U.S. Pat. No. 4,343,301 describes generating high energy by intersecting two ultrasound beams within any single fixed point of the body, including the skull. While it is not proven that such an application of ultrasound would do anything except heat or destroy tissue, there is recent evidence that application of focused ultrasound to brain slices, subjected to simultaneous electrical stimulation, can change the electrical currents in the slices. However, because two ultrasound beams cannot be focused within the skull, because of the complexity of bone density and bone structure, it is not possible to focus such a two-beam device in the brain tissue.

Some companies have produced ultrasonic devices that use multiple beams. See G. T. Clement, et al., *Physics in Medicine and Biology* (December 2000), Vol. 45, no. 12, pp. 3707-3719. By coordinating the amplitude and the phase of the ultrasound beams generated by multiple sources via computer multi-beam devices, algorithms can be developed to adjust the bone dispersion of the beam and focus the ultrasound within the brain tissue. These devices are to be used as ultrasonic knives within the brain for the destruction of tumors, for example. However, they cannot be used to modify the electrical and electromagnetic currents within the brain circuits without harming the surrounding tissue.

SUMMARY OF THE INVENTION

It is an object of the invention to provide methods for modifying electrical currents in a live neuronal circuit of a mammal, preferably a human. The modification is accomplished by applying a focused ultrasound pulse (FUP) under the guidance of a brain-imaging system such as a functional magnetic resonance imaging (fMRI) system, a vector-electroencephalograph (V-EEG), or a positron emission tomograph (PET), preferably fMRI. The application of FUP is generally via multiple ultrasound transducers that are housed in a cap worn by a patient. It is simultaneous with the use of the brain-imaging system. The application of different frequencies and phases of FUP to the brain circuits will generate a signal that will be captured by fMRI. At that time, changes in circuits will be assessed. This will permit adjustment of the focus of the FUP and of the location of the FUP, or the use of multiple focuses, to achieve the maximum modification of the circuit. The changes in the circuit are useful for research, diagnosis and treatment.

In the present embodiments, there is provided a method of treating psychiatric, neurological and neuroendocrine disorders in a mammal through application of FUPs. The treatment is accomplished by applying a focused ultrasound pulse (FUP) to a tissue of the mammal, and the applied FUP uses a variation in frequency to disrupt or activate a tissue function. Monitoring is performed through a tissue image from an imaging system during the application of the FUP. The tissue can be the brain of the mammal or any other body tissue of the mammal.

It is a further object of the methods to diagnose and treat specific psychiatric, neurological, and neuroendocrine conditions. Examples of such conditions include, but are not limited to, Obsessive Compulsive Disorder and its spectrum, Post Traumatic Stress Disorder, Depression, Bipolar Disorder, Social Anxiety Disorder, Psychotic Disorders, Panic Disorder, Ticks, Chronic Pain Syndrome, Insomnia, Chronic Fatigue Syndrome, Insomnia, Stress and Obesity, and other conditions apparent to one of ordinary skill in the art.

In further embodiments, there is provided a method of treating a mammal comprising the steps of administering a pharmaceutical medication to the mammal, assessing the pharmaceutical medication in the mammal with an imaging system to determine when the pharmaceutical medication distributes to or reaches a target location in the mammal, applying a focused ultrasound pulse (FUP) to the target location in the mammal to alter the pharmaceutical medication at the target location, and assessing the response from to the medication from the target location with an image from the imaging system during the application of the FUP. The alteration may cause a change in property of the pharmaceutical medication, such as for example, the chemical activity, composition and viscosity. In an embodiment, the alteration changes the pharmaceutical medication to an active form. Furthermore, the treatment of applying a FUP to a tissue of the mammal in combination with the administering of a pharmaceutical medication to the mammal and altering the pharmaceutical medication at a target location, all the while assessing the tissue activity and/or response through the imaging system, provides a novel manner of treating a number of disorders contemplated herein.

BRIEF DESCRIPTION OF THE DRAWINGS

A detailed description of embodiments of the invention will be made with reference to the accompanying drawings, wherein numerals designate corresponding parts in the several figures.

DETAILED DESCRIPTION

Figure 1:
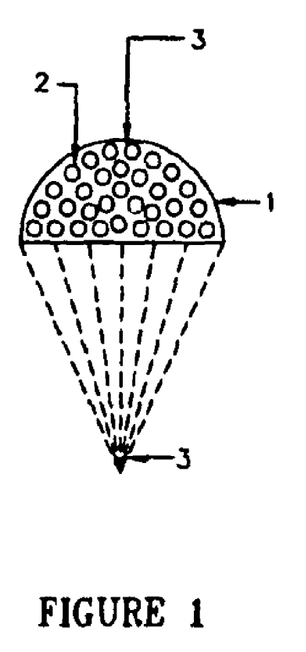
FIG. 1 illustrates an FUP device according to one embodiment of the invention. Shown is a modified multi-transducer cap, capable of focusing ultrasound in the skull and delivering the FUP signal to a specific target in the brain.

FIG. 1 illustrates a preferred embodiment of a focused ultrasound pulse (FUP) device. A cap 1 houses multiple ultrasound transducers 2, preferably 300-1000 transducers. The FUP device is preferably a multi-beam ultrasonic device, which is coordinated via computer with conventional brain-imaging system, such as a focused magnetic resonance imaging (fMRI) system, a vector-electroencephalograph (V-EEG) or a positron emission tomograph (PET), preferably an fMRI system. An example of a preferable multi-beam ultrasonic device is an ultrasound knife. The transducers are regulated via a computer capable of focusing the ultrasound waves into a specific point 3. The cap and transducers are preferably made from a non-ferromagnetic material, a material that has a very low permeability and residual magnetism and hysterisis, such as copper. The use of a non-ferromagnetic material reduces fMRI field distortion and thereby reduces distortion of the image, permitting the application of FUP concurrently with the use of fMRI. By concurrent, it is meant that one applies an FUP within 1 millisecond to 10 seconds before or after using the fMRI system to image the brain.

Figure 2:
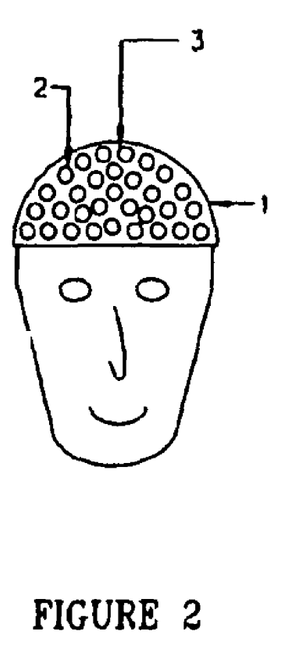
FIG. 2 illustrates how the cap of FIG. 1 can be placed on the head of a human subject.

FIG. 2 illustrates how the cap can be placed on the head of a human subject. A computer, which is coupled to the FUP device, controls the parameters of the FUP, including focus, frequency, phase and amplitude. Through user interaction with the computer, the FUP device is capable of producing a focused ultrasound pulse in a specific point within the brain. The FUP's focus is preferably 2 or more centimeters deep and 0.5-1000 mm in diameter, and more preferably 2-12 cm deep and 0.5-2 mm in diameter. The specific point is determined by a conventional brain-imaging system, preferably an fMRI system, which provides information about brain form and density. FUP software is preferably coordinated with fMRI software for precise positioning and coordination of the focused signal. The changes in activity within the neuronal circuits are determined by monitoring the changes in the brain image produced by the fMRI before the application of FUP and during and after the application of FUP. These changes are used to determine exactly where the FUP focus was in the brain and the functional connectivity between the focus and surrounding brain centers. The specific point may be confirmed using the addition of a computed tomography (CT) scan, which provides information about bone density and structure of the skull and brain. The focus of the FUP may then be modified to direct it into a different point of the brain.

A single FUP may be applied to a single live neuronal circuit. Multiple FUPs may be applied to the same live neuronal circuit. Additionally, a single FUP may be applied to multiple live neuronal circuits, and multiple FUPs may be applied to multiple live neuronal circuits.

FUP given in different frequency, phase and amplitude will produce different effects on neuronal circuits and centers. Low frequencies, below 300 Hz, will decrease the firing of the centers and inhibit or disrupt the neuronal circuits. High frequencies, 500 Hz to 5 MHz, will produce activation of firing of neuronal centers and activation of the circuits. In either case, the FUP will modify physiological properties in the circuits. This will happen both when the FUP is applied to the centers and when the FUP is applied to the white matter.

Repeated application of the FUP to neuronal circuits will cause long-term or permanent changes to the circuits. The modification of the circuits using FUP will be used for the treatment of psychiatric, neurological and neuroendocrine disorders. Examples of such diseases include, but are not limited to, Obsessive Compulsive Disorder (and its spectrum), Post Traumatic Stress Disorder, Depression, Bipolar Disorder, Social Anxiety Disorder, Psychotic Disorders, Panic Disorder, Ticks, Chronic Pain Syndrome, Insomnia, Chronic Fatigue Syndrome, Insomnia, Stress, Obesity, and other conditions apparent to one of ordinary skill in the art. This will be done by repeated assessment and modification of changes in neuronal flow or field activity under the guidance of specific brain imaging techniques, such as fMRI, V-EEG, or PET.

In one embodiment, there is provided a method of treating psychiatric, neurological and neuroendocrine disorders in a mammal by applying a focused ultrasound pulse (FUP) to a tissue of the mammal, and the applied FUP uses a variation in frequency to disrupt or activate a tissue function, and monitoring the tissue through a tissue image from an imaging system during the application of the FUP. The tissue can be that in the brain or another portion of the body. In specific embodiments, the tissue is that of a brain region such as the hypothalamus or medulla oblongata. In such embodiments, the applied FUP uses a low frequency to disrupt the neuronal circuits or a high frequency to activate the neuronal circuits of the brain region such that the disruption or activation results in a modulation of a bodily reaction. The FUP application and the modulation can be monitored through a brain image from the imaging system. The application of FUP may also be applied to at least one other live neuronal circuit within the brain region concurrently.

Application of FUP to the hypothalamus, and more specifically to a hypothalamic nuclei, can modify the release of natural hormones and cause either an increase or decrease in release of a hypothalamic hormone. The hypothalamic hormone can be any of the following: corticotrophin-releasing hormone (CRH), dopamine, gonadotropin-releasing hormone, growth hormone-releasing hormone, melatonin, oxytocin, somatostatin, thyrotropin-releasing hormone, vasopressin, and mixtures thereof. The hypothalamic nuclei can be from the anterior nuclei, tuberal nuclei or posterior nuclei. The modification of release of natural hormones can help treat a number of disorders such as sexual disorder, menstrual disorder, diabetes, growth disorder, blood pressure disorder, thyroid disorder, skin disorder, and wake sleep cycle disorder. Gonadotropin-releasing hormone (GnRH), for example, can cause increases in testosterone and estrogen in males and females, which in turn can increase sexual desire, cause loss of weight, increase energy and decrease anxiety and depression. Increase in estrogen can also prevent osteoporosis, improve physiological and psychological symptoms associated with menstrual dysfunctions. Increase in growth hormone can help increase and improve the energy and height of people, as well as delay aging. Changes in Antidiuretic hormone (ADH) and Oxytocin can modify blood pressure and electrolyte imbalance. Thyrotropin-releasing hormone (TRH) regulates the release of thyroid hormone and modification of TRH levels can help in treatment of symptoms of hyper and hypo-thyroidism.

Neuroendocrine-immune interactions are regulated by CRH indirectly, through activation of a global stress response, and directly, through pro-inflammatory actions on peripheral immune functions. Neuroimmunological data have demonstrated that CRH activation of the sympathetic nervous system is essential in mediating the link between the brain and immune function. CRH is distributed in the brain and spinal cord, adrenal medulla, testes, ovaries, gastrointestinal tract, pancreas, myometrium, endometrium, placenta, and diverse inflammatory sites. Traditionally, hypothalamic CRH has been considered to act indirectly in an anti-inflammatory fashion, since the end product of the hypothalamic-pituitary-adrenal axis is cortisol, a well-known anti-inflammatory compound. Thus, activation of CRH will influence immunity and can treat immunological disorders without the negative side effects of external or synthetic hormonal therapy. A modification of the release of corticotrophin-releasing hormone wherein the hormone is increased may be used to treat a number of immunological disorders. It is also contemplated, however, that a decrease in CRH may help treat other disorders. For example, where the release of corticotrophin-releasing hormone is decreased, this may help treat opportunistic inflammations and fungal infections as well as beneficially affect some forms of cancer.

Application of FUP to the medulla oblongata can modulate an effect on the sympathetic or parasympathetic nervous system. This embodiment may be used to treat peripheral neuronal disorders such as bowel disorders, ulcers, inflammatory bowel syndrome disorder, irritable bowel syndrome disorder, arrhythmia, and high blood pressure The supra thalamic nuclei inputs into the pineal gland and can modify the level of melatonin, the hormone that regulates pigmentation of the skin and the sleep wake cycle. Modification of the pineal gland through FUP application to the supra thalamic nuclei may normalize sleep-wake cycle and treat some skin disorders such as excessive pigmentation.

Figure 3:
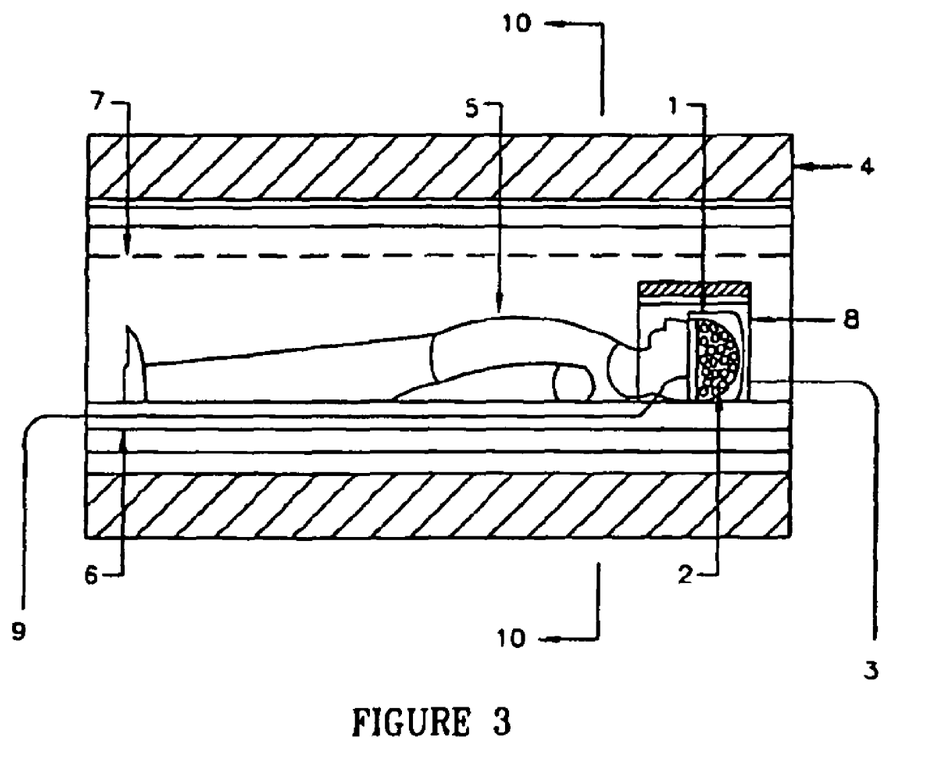
FIG. 3 illustrates a system in accordance with an embodiment of the present invention in which the FUP device is being used in conjunction with the brain imaging system, here shown as fMRI.

FIG. 3 illustrates the FUP being used in conjunction with a fMRI system. The fMRI system is preferably a typical GE build cylindrical magnet 4. The patient 5 preferably lies on a sliding platform 6 inside of the magnetic cavity 7. The imaging coil 8, which has been placed over the head of the patient, detects the magnetic resonance field generated by rotation of the magnet 4. The field signals detected by the imaging coil are preferably transmitted to the processing electronics outside the magnet. As a result of the fMRI system's computer analysis, a functional image of the brain is generated.

Figure 4:
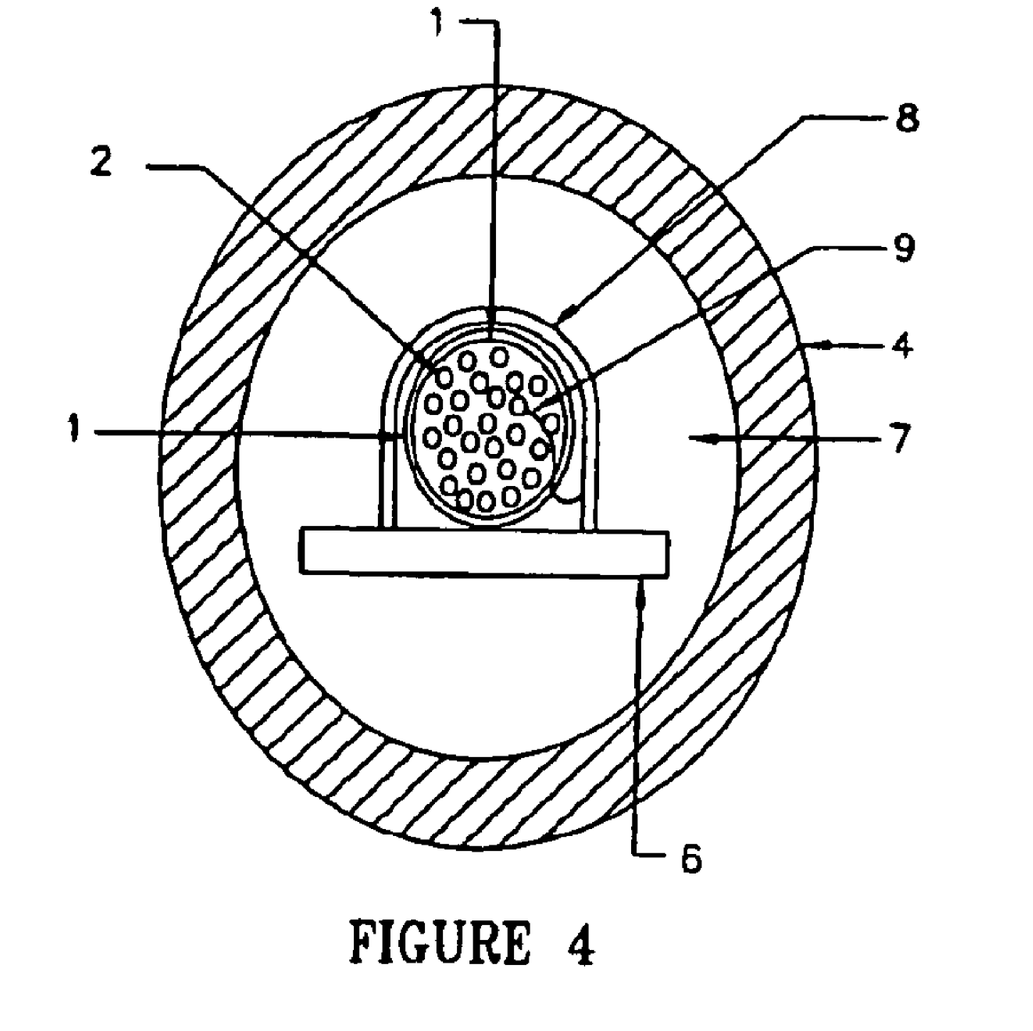
FIG. 4 illustrates a perspective of the right side of the system shown in FIG. 3, looking down on the head of the human subject.

FIG. 4 illustrates a cross-sectional view of FIG. 3, from a perspective looking down on the head of the patient, as shown by reference numeral 10 in FIG. 3. The cap 1 containing the FUP transducers 2 is preferably on the head of the patient. The imaging coil 8 is preferably placed above the FUP cap. A cable 9 connects the FUP cap with the transducers to the computer, which is kept outside of the room, controlling the FUP. The FUP device is also connected to MRI processing electronics. The FUP device generates FUP pulses that cause activation or deactivation of specific neuronal centers or circuits. The fMRI signal is modified in specific locations. This modification is captured and used to adjust the FUP transducers to achieve better focus, different position, or different influence on the neuronal circuit by modification of the frequency of the waves, frequency of the pulse, intensity of the pulse, or the phase of the waves.

Figure 5:
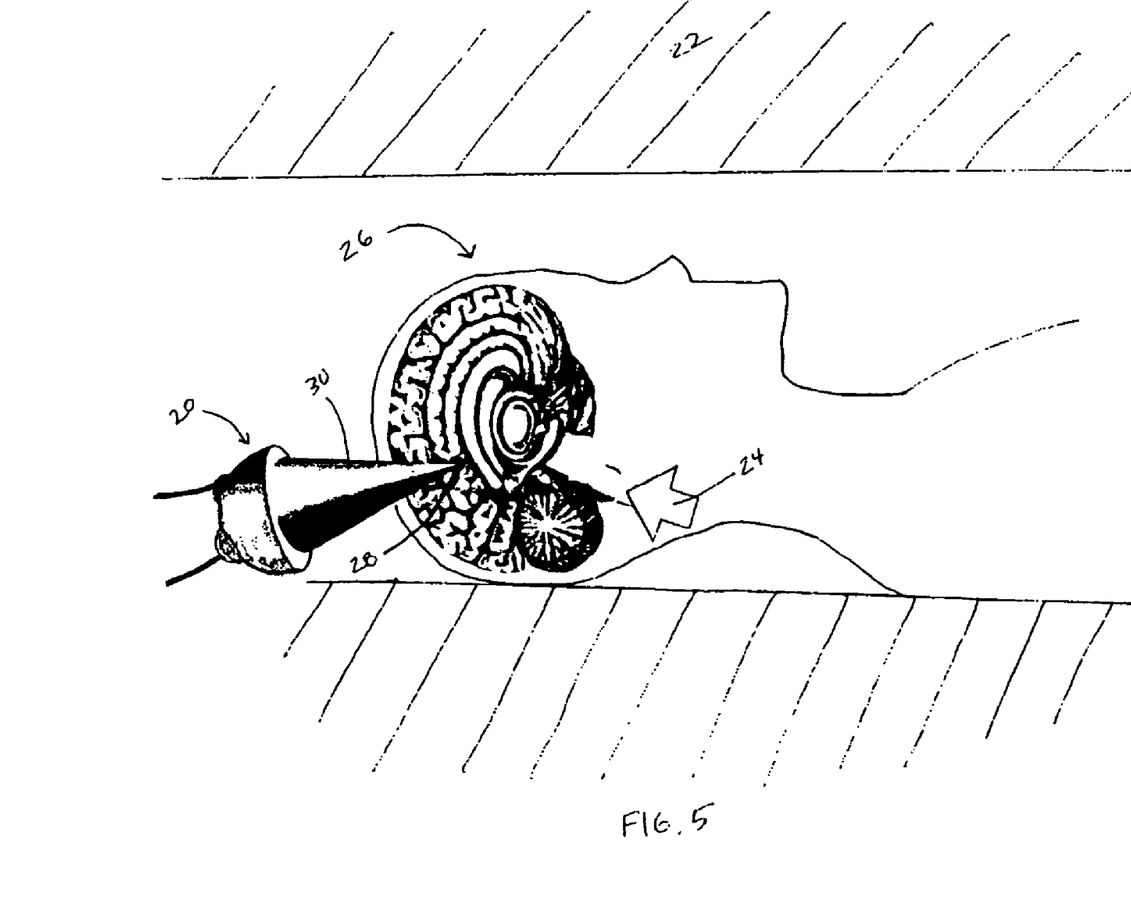
FIG. 5 illustrates a system in accordance with an embodiment of the present invention in which the FUP device is being used in conjunction with an imaging system to alter an administered pharmaceutical medication.

FIG. 5 illustrates a system in accordance with an embodiment of the present invention in which the FUP device 20 is being used in conjunction with an imaging system 22 to alter an administered pharmaceutical medication 24 and assess a bodily reaction from the altered pharmaceutical medication. In this embodiment, a method of treatment is provided in which a pharmaceutical medication 24 is administered to the mammal 26, for example, through ingestion or injection. The pharmaceutical medication 24 is allowed to distribute to a target location 28 in the mammal 26, for example, a focal point in the brain. The target location can be the brain of the mammal or any other body tissue of the mammal.

Once it is determined that the medication 24 has distributed to the target location 28, a FUP 30 is applied to the target location 28 in the mammal 26 to alter the pharmaceutical medication 24. The alteration of medication during and after the application of the FUP 30 can be assessed with images from an imaging system 22. The imaging system may be selected from the group consisting of a functional magnetic resonance image (fMRI) system; a vector-electroencephalogram (V-EEG), and a positron emission tomography (PET). For example, in one embodiment, the pharmaceutical medication is administered to a subject in a non-toxic or non-active form. The medication is allowed to distribute and once the target location is reached, the FUP is applied to the focal point to alter the pharmaceutical medication. In embodiments, imaging techniques can be used to monitor and/or guide the medication as it reaches a target location or specific focal point, be it in the brain or another body tissue. One or more FUPs may be applied as needed and the alteration of the medication may be assessed through the imaging system. The frequency and phase of the FUP may also be changed to change the focus of any subsequently applied FUPs at the target location. Bodily reactions to the pharmaceutical medication after the applied FUP at the target location are assessed with an image from the imaging system.

The alteration causes a change in property of the pharmaceutical medication—the property selected, for example, from the group consisting of chemical activity, composition and viscosity. In a particular embodiment, the alteration activates the pharmaceutical medication. By activating the medication with FUP once it is at a specific focal point in the body, specific medication that could not otherwise access the focal point without harmful effects can do so more safely. For example, an anti-cancer drug can be injected or orally ingested in non-active and non-toxic form. Subsequently, the drug can be activated once it is delivered precisely to the location of the brain tumor. FUP application is then used to alter the drug into an activate form, thus avoiding the toxicity from the drug in other parts of the body. The delivery and effect of the drug can be observed on the imaging. Similarly, a Parkinson patient can be administered a medication, such as a dopamine activating peptide, in an inactive form and subsequently activated using FUP near basal ganglia circuits causing effect only in that location. This manner of delivery will permit relieving the symptoms without suffering the usual side effects of dopaminergic drugs. In another example, the method may be used to deliver medication across the blood/brain barrier. Many substances cannot bypass the blood-brain barrier. Certain proteins such as liposomal proteins, however, can bypass the blood-brain barrier, so by covering a pharmaceutical medication with the protein, the medication can pass through the barrier. Once the medication has passed through the barrier, applied FUP can be used to destroy the liposomal protein. Moreover, this method can be used for drug delivery or activation within the brain or within any other tissue in the body.

Mechanical forces produced by frequency 300 Hz or higher can change properties of chemical substances within the FUP focus. These properties include, for example, a change in chemical activity, composition or viscosity. In particular, application of FUP at this frequency range can change the chemical structure by splitting the chemical structure, such as that of protein, RNA, DNA or peptides, into an active and inactive form. The change in the chemical properties or activity can be effected at the target location and can be assessed through imaging. The reaction of the tissue, neuronal centers or neuronal circuits to chemical substance activated by FUP will also be observed on the imaging.

The use of FUP in combination with fMRI or other imaging devices can provide a variety of diagnostic, research and therapeutic benefits. The invention can be used to create a functional map of the brain in response to modification of the neuronal circuits. It can also allow one to observe the functional connectivity within the brain of normal subjects as well as in the brain of the subjects suffering from various neurological conditions, such as the ones identified above. The present embodiments can also be used treat these conditions, and may be used concurrently with the pharmaceutical agents commonly prescribed for them. For example, the treatment of applying a FUP to a tissue of the mammal in combination with the administering of a pharmaceutical medication to the mammal and altering the pharmaceutical medication at a target location, all the while assessing the tissue activity and/or response through the imaging system, provides a novel manner of treating a number of disorders contemplated herein.

Development of the functional brain maps can significantly improve our understanding of the operation of the brain in normal subjects and in different diseased states. Unlike the use of transcranial magnetic stimulation (TMS), which can only read a brain tissue depth of about 1 to 2 cm, the FUP is able to reach brain tissue much deeper, 2 or more centimeters into the brain, for example, from about 2 to about 12 cm. Furthermore, the FUP can also produce a focus of energy that will be only from about 0.5 to about 2 mm in diameter, as opposed to about 2-3 cm. attainable by TMS.

The present embodiments can be used for the evaluation of the outcome of a variety of treatments. For example, the functional maps of the brain, such as those mapping functions of different areas of the brain after application of the FUP, may be constructed using fMRI before and after a particular treatment. If after the treatment the functional reactivity of a certain neuronal circuit becomes similar to that of normal controls, then that may be an indicator of the efficacy of a treatment. In the same way, the present embodiments can be used to determine when the activity of the certain neuronal areas reaches a specific level. The repeated application of FUP may modify the circuits in such a way that their functionality becomes the same as in normal subjects. Repeated application together with continuous fMRI monitoring may help to determine the most efficient, reliable and fast ways to achieve the normalization of neuronal structure and neuronal circuit function. As such, the present embodiments may make the FUP more efficient by determining the best phase, intensity and frequency of the pulse, as well as the best position of the focus or multiple focuses for diagnosis and treatment of the above-mentioned conditions.

In addition, the present embodiments can be used for the development of pharmaceuticals. For example, the functional maps of the brain could be created using fMRI before, during, and after a particular pharmaceutical is administered to a patient. If, after administration of the pharmaceutical, the functional reactivity of a certain neuronal circuit becomes similar to that of normal controls, then that may be an indicator of the efficacy of the medication.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects illustrative and not restrictive, the scope of the invention being indicated by the appended claims, rather than the foregoing description, and all changes that come within the meaning and range of equivalency of the claims are therefore intended to be embraced therein.

What is claimed is:

1. A method of treating psychiatric, neurological and neuroendocrine disorders in a mammal, the method comprising the steps of:
applying a focused ultrasound pulse (FUP) to a live neuronal circuit in a tissue of the mammal, and the applied FUP uses a variation in pulsation parameter frequency to disrupt or activate a neuronal circuit function such that a naturally occurring hormone is released in the live neuronal circuit and in an organ connected to the live neuronal circuit and a level of the naturally occurring hormone is modulated; and
monitoring a tissue image including the live neuronal circuit from an imaging system during the application of the FUP.

2. The method of claim 1, wherein the mammal is a human.

3. The method of claim 1, wherein the tissue is a brain of the mammal.

4. The method of claim 1, wherein the imaging system is selected from the group consisting of a functional magnetic resonance image (fMRI) system; a vector-electroencephalogram (V-EEG), and a positron emission tomograph (PET).

5. The method of claim 1, further comprising the step of:
administering a pharmaceutical medication to the mammal; and
assessing the tissue image from the imaging system after the administration of the pharmaceutical medication.

6. The method of claim 1, wherein the disruption or activation of the neurona circuit releases naturally occurring hormones in another neuronal circuit that is connected to the live neuronal circuit.

7. The method of cairn 1, wherein the disruption or activation of the neuronal circuit releases naturally occurring hormones in a gland that is connected to the live neuronal circuit.

8. A method of treating psychiatric, neurological and neuroendocrine disorders in a mammal, the method comprising the steps of:
applying a focused ultrasound pulse (FUP) to a tissue of a mammal, and the applied FUP uses a variation in frequency to disrupt or activate a tissue function such that a hormone level is modulated; and
monitoring a tissue image from an imaging system during the application of the FUP, wherein the tissue is a brain of the mammal and the FUP is applied to a live neuronal circuit within a brain region of the mammal, the brain region being selected from the group consisting of a hypothalamus and a medulla oblongata, and the applied FUP uses a low frequency to disrupt the neuronal circuits or a high frequency to activate the neuronal circuits, and wherein the brain image is monitored from the imaging system during the application of the FUP.

9. The method of claim 8, wherein the FUP is applied to the hypothalamus and the modulation is an increase or decrease in release of a hypothalamic hormone.

10. The method of claim 9, wherein the disorders are selected from the group consisting of sexual disorder, menstrual disorder, diabetes, growth disorder, blood pressure disorder, thyroid disorder, skin disorder, and wake sleep cycle disorder.

11. The method of claim 8, wherein the FUP is applied to a hypothalamic nuclei in the hypothalamus, the hypothalamic nuclei being selected from the group consisting of an anterior nuclei, a tuberal nuclei and a posterior nuclei.

12. The method of claim 8, wherein the hypothalamic hormone is selected from the group consisting of corticotrophin-releasing hormone, dopamine, gonadotropin-releasing hormone, growth hormone-releasing hormone, metonin, oxytocin, somatostatin, thyrotropin-releasing hormone, vasopressin, and mixtures thereof.

13. The method of claim 12, wherein the release of corticotrophin-releasing hormone is increased.

14. The method of claim 13, wherein the disorders are selected from the group consisting of rheumatoid arthritis, ulcerative colitis, lupus, and myelofibrosis.

15. The method of claim 12, wherein the release of corticotrophin-releasing hormone is decreased.

16. The method of claim 15, wherein the disorders are selected from the group consisting of cancer, opportunistic inflammations and fungal infections.

17. The method of claim 8, further comprising the step of:
applying at least one additional FUP to at least one other live neuronal circuit within the brain region.

18. The method of claim 8, wherein the FUP is applied to the medulla oblongata and the modulation is an effect on the sympathetic or parasympathetic nervous system.

19. The method of claim 18, wherein the disorders are selected from the group consisting of bowel disorders, ulcers, inflammatory bowel syndrome disorder, irritable bowel syndrome disorder, arrhythmia, and high blood pressure.

20. A method of treating psychiatric, neurological and neuroendocrine disorders in a mammal, the method comprising the steps of:
applying a focused ultrasound pulse (FUP) to a live neuronal circuit, where the applied FUP uses a low frequency to disrupt the neuronal circuits or a high frequency to activate the neuronal circuits;
monitoring a brain image from a brain imaging system during the application of the FUP;
administering a pharmaceutical medication to the mammal;
allowing the pharmaceutical medication to distribute to a target location in the brain of the mammal;
applying a second FUP to the target location in the mammal to alter the pharmaceutical medication at the target location; and
assessing a response to the pharmaceutical medication from the mammal with the brain image from the imaging system after the application of the second FUP.

21. The method of claim 20 further including monitoring the pharmaceutical medication in the mammal with the imaging system to determine when the pharmaceutical medication is distributed to the target location in the mammal.

22. The method of claim 20, wherein the focus of the FUP is about 2 or more centimeters into the brain from the exterior of the skull.

23. The method of claim 20, wherein the focus of the FUP is from about 2 cm to about 12 cm into the brain from the exterior of the skull.

24. The method of claim 20, wherein the frequency of the FUP is less than 300 Hz.

25. The method of claim 20, wherein the frequency of the FUP is from about 500 Hz to about 5 MHz.

26. The method of claim 20, wherein a diameter of the focus area of the FUP is about 0.5 mm.

27. The method of claim 20, further comprising the steps of:
adjusting a frequency and phase of the second FUP to change the focus of the second FUP; and
applying a third FUP to the target location.

28. The method of claim 20, further comprising the step of running a pre-timed computed tomography (CT) scan to determine bone density and structure of bone surrounding the brain.

* * * * *